(12) United States Patent
Marziali et al.

(10) Patent No.: US 8,877,028 B2
(45) Date of Patent: Nov. 4, 2014

(54) SYSTEM AND METHODS FOR DETECTION OF PARTICLES

(75) Inventors: Andrea Marziali, North Vancouver (CA); Jason Donald Thompson, Vancouver (CA)

(73) Assignee: The University of British Columbia, Vancouver (CA)

( * ) Notice: Subject to any disclaimer, the term of this patent is extended or adjusted under 35 U.S.C. 154(b) by 345 days.

(21) Appl. No.: 13/264,988

(22) PCT Filed: Apr. 21, 2010

(86) PCT No.: PCT/CA2010/000624
§ 371 (c)(1),
(2), (4) Date: Oct. 17, 2011

(87) PCT Pub. No.: WO2010/121381
PCT Pub. Date: Oct. 28, 2010

(65) Prior Publication Data
US 2012/0048735 A1    Mar. 1, 2012

Related U.S. Application Data

(60) Provisional application No. 61/202,932, filed on Apr. 21, 2009.

(51) Int. Cl.
*G01N 27/447* (2006.01)
(52) U.S. Cl.
USPC ............ 204/457; 204/458; 204/608; 204/609
(58) Field of Classification Search
USPC .......... 204/458, 457, 547, 608, 609, 615, 643
See application file for complete search history.

(56) References Cited

U.S. PATENT DOCUMENTS

| | | | |
|---|---|---|---|
| 4,148,703 A | 4/1979 | Trop et al. |
| 4,390,403 A | 6/1983 | Batchelder |
| 4,390,404 A | 6/1983 | Esho et al. |
| 4,732,656 A | 3/1988 | Hurd |

(Continued)

FOREIGN PATENT DOCUMENTS

| | | | |
|---|---|---|---|
| CA | 2552262 A1 | 8/2005 |
| CA | 2523089 A1 | 4/2006 |

(Continued)

OTHER PUBLICATIONS

Anonymous, "Nucleic Acid Purification + Technical Presentation," Boreal Genomics, http://www.borealgenomics.com/technology/purification/, Jan. 24, 2010.

(Continued)

*Primary Examiner* — J. Christopher Ball
(74) *Attorney, Agent, or Firm* — Thomas C. Meyers; Brown Rudnick LLP

(57) ABSTRACT

Particles of interest such as DNA, RNA may be detected in trace quantities by subjecting the particles to concentration by scodaphoresis, detecting a signal indicative of the presence of the particles in a scodaphoresis focus spot and performing phase-sensitive detection on the signal using a reference signal tied to the scodaphoresis fields. Specificity may be enhanced by using a medium having high affinity for the particles and/or markers having specific affinity for the target particles. In some embodiments a fluorescence signal is detected and subjected to phase-sensitive analysis. The signal may be detected by a camera or other imaging system.

34 Claims, 10 Drawing Sheets

(56) References Cited

U.S. PATENT DOCUMENTS

| | | |
|---|---|---|
| 4,911,817 A | 3/1990 | Kindlmann |
| 4,971,671 A | 11/1990 | Slater et al. |
| 5,084,157 A | 1/1992 | Clark et al. |
| 5,185,071 A | 2/1993 | Serwer et al. |
| 5,286,434 A | 2/1994 | Slater et al. |
| 5,384,022 A | 1/1995 | Rajasekaran |
| 5,453,162 A | 9/1995 | Sabanayagam et al. |
| 5,609,743 A | 3/1997 | Sasagawa et al. |
| 5,641,628 A | 6/1997 | Bianchi |
| 5,938,904 A | 8/1999 | Bader et al. |
| 6,036,831 A | 3/2000 | Bishop |
| 6,110,670 A | 8/2000 | Van Broeckhoven et al. |
| 6,146,511 A | 11/2000 | Slater et al. |
| 6,193,866 B1 | 2/2001 | Bader et al. |
| 6,258,540 B1 | 7/2001 | Lo et al. |
| 6,693,620 B1 | 2/2004 | Herb et al. |
| 6,824,664 B1 | 11/2004 | Austin et al. |
| 6,827,830 B1 | 12/2004 | Slater et al. |
| 6,893,546 B2 | 5/2005 | Jullien et al. |
| 6,927,028 B2 | 8/2005 | Dennis et al. |
| 7,175,747 B2 | 2/2007 | Bayerl et al. |
| 7,198,702 B1 | 4/2007 | Washizu et al. |
| 7,371,533 B2 | 5/2008 | Slater et al. |
| 7,427,343 B2 | 9/2008 | Han et al. |
| 7,442,506 B2 | 10/2008 | Dhallan |
| 7,452,668 B2 | 11/2008 | Boles et al. |
| 7,838,647 B2 | 11/2010 | Hahn et al. |
| 7,888,017 B2 | 2/2011 | Quake et al. |
| 8,008,018 B2 | 8/2011 | Quake et al. |
| 8,182,666 B2 | 5/2012 | Marziali et al. |
| 8,195,415 B2 | 6/2012 | Fan et al. |
| 2001/0045359 A1 | 11/2001 | Cheng et al. |
| 2002/0036139 A1 | 3/2002 | Becker et al. |
| 2002/0081280 A1 | 6/2002 | Curiel et al. |
| 2002/0119448 A1 | 8/2002 | Sorge et al. |
| 2002/0179445 A1 | 12/2002 | Alajoki et al. |
| 2003/0027178 A1 | 2/2003 | Vasmatzis et al. |
| 2003/0215855 A1 | 11/2003 | Dubrow et al. |
| 2005/0164241 A1 | 7/2005 | Hahn et al. |
| 2005/0164402 A1 | 7/2005 | Belisle et al. |
| 2005/0247563 A1 | 11/2005 | Shuber et al. |
| 2005/0247564 A1 | 11/2005 | Volkel et al. |
| 2007/0215472 A1 | 9/2007 | Slater et al. |
| 2007/0218494 A1 | 9/2007 | Slater et al. |
| 2008/0108063 A1 | 5/2008 | Lucero et al. |
| 2008/0314751 A1 | 12/2008 | Bukshpan et al. |
| 2009/0120795 A1 | 5/2009 | Marziali et al. |
| 2009/0139867 A1 | 6/2009 | Marziali et al. |
| 2009/0152116 A1 | 6/2009 | Boles et al. |
| 2010/0285537 A1 | 11/2010 | Zimmermann |
| 2011/0048950 A1 | 3/2011 | Marziali et al. |
| 2011/0245482 A1 | 10/2011 | Hahn et al. |
| 2011/0272282 A1 | 11/2011 | Marziali et al. |
| 2012/0048735 A1 | 3/2012 | Marziali et al. |
| 2012/0160682 A1 | 6/2012 | Marziali et al. |
| 2012/0199481 A1 | 8/2012 | Marziali et al. |

FOREIGN PATENT DOCUMENTS

| | | |
|---|---|---|
| CA | 2496294 A1 | 8/2006 |
| CA | 2641326 A1 | 8/2006 |
| CA | 2713313 A1 | 8/2009 |
| CA | 2742460 A1 | 5/2010 |
| EP | 0356187 A2 | 2/1990 |
| EP | 1720636 A1 | 11/2006 |
| EP | 1859249 A0 | 11/2007 |
| EP | 2238434 A0 | 10/2010 |
| EP | 2458004 A1 | 5/2012 |
| GB | 2249395 A | 5/1992 |
| JP | 7-167837 A | 7/1995 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 9945374 A2 | 9/1999 |
| WO | 0131325 A1 | 5/2001 |
| WO | 0242500 A2 | 5/2002 |
| WO | 03019172 A2 | 3/2003 |
| WO | 2005072854 A1 | 8/2005 |
| WO | 2006063625 A1 | 6/2006 |
| WO | 2006081691 A1 | 8/2006 |
| WO | 2007092473 A2 | 8/2007 |
| WO | 2009094772 A1 | 8/2009 |
| WO | 2010051649 A1 | 5/2010 |
| WO | 2010/104798 A1 | 9/2010 |
| WO | 2010121381 A1 | 10/2010 |
| WO | 2013002616 A2 | 1/2013 |

OTHER PUBLICATIONS

Asbury, et al., "Trapping of DNA by dielectrophoresis", Electrophoresis, 2002, 23:2658-2666.

Asbury, et al., "Trapping of DNA in Nonuniform Oscillating Electric Fields", Biophysical Journal, 1998, 74:1024-1030.

Astumian, et al., "Fluctuation Driven Ratchets: Molecular Motors", Physical Review Letters, 1994, 72(11):1766-1769.

Bier, Martin, et al., "Biasing Brownian Motion in Different Directions in a 3-State Fluctuating Potential and an Application for the Separation of Small Particles", Physical Review Letters, 1996, 76(22):4277-4280.

Broemeling, D., et al., "An Instrument for Automated Purification of Nucleic Acids from Contaminated Forensic Samples", JALA 2008, 13, 40-48.

Carle, G.F., et al., "Electrophoretic Separations of Large DNA Molecules by Periodic Inversion of the Electric Field", Science, 1986, 232(4726):65-68.

Chacron, M.J., et al., "Particle trapping and self-focusing in temporarily asymmetric ratchets with strong field gradients", Physical Review E, 1997, 56(3):3446-3450.

Chakrabarti, Subrata, et al., "Highly Selective Isolation of Unknown Mutations in Diverse DNA Fragments: Toward New Multiplex Screening in Cancer", American Association for Cancer Reserch, 2000, 60:3732-3737.

Chan, K.C. Allen, et al., "Size Distributions of Maternal and Fetal DNA in Maternal Plasma", Molecular Diagnostics and Genetics, Clinical Chemistry, 2004, 50(1):88-92.

Chu, Gilbert, "Bag model for DNA migration during pulsed-field electrophoresis", Proc. Natl. Acad. Sci., 1991, 88:11071-11075.

European Search Report corresponding to EP11004417, Mar. 29, 2012, 4 pages.

Frumin, L.L., et al., "Anomalous size dependence of the non-linear mobility of DNA", in PhysChemComm, 2000, 11 (3):61-63.

Frumin, L.L., et al., "Nonlinear focusing of DNA macromolecules", Physical Review E—Statistical, Nonlinear and Soft Matter Physics, 2001, 64:021902-1-5.

Griess, Gary A., et al., "Cyclic capillary electrophoresis", Electrophoresis, 2002, 23:2610-2617.

International Preliminary Report on Patentability corresponding to PCT/CA2005/000124, Aug. 7, 2006, 8 pages.

International Preliminary Report on Patentability corresponding to PCT/CA2006/000172, Aug. 7, 2007, 8 pages.

International Preliminary Report on Patentability corresponding to PCT/CA2009/000111, Aug. 3, 2010, 9 pages.

International Search Report dated Feb. 23, 2010 corresponding to PCT/CA2009/001648, 6 pages.

International Search Report for PCT/CA2006/000172, International Searching Authority, Jun. 2, 2006, 4 pages.

Jorgez, Carolina J., et al., "Quantity versus quality: Optimal methods for cell-free DNA isolation from plasma of pregnant women", American College of Medical Genetics, 2006, 8(10):615-619.

(56) References Cited

OTHER PUBLICATIONS

Kitzman, Jacob O., et al., "Noninvasive Whole-Genome Sequencing of a Human Fetus", Sci Transl Med 4, 137ra76 (2012); DOI: 10.1126/scitranslmed.3004323, 9 pages.

Kopecka, K., et al., "Capillary electrophoresis sequencing of small ssDNA molecules versus the Ogston regime: Fitting data and interpreting parameters", Electrophoresis, 2004, 25(14):2177-2185.

LaLande, Marc, et al., "Pulsed-field electrophoresis: Application of a computer model to the separation of large DNA molecules", Proc. Natl. Acad. Sci. USA, 1987, 84:8011-8015.

Lun, Fiona M. F., et al., "Microfluidics Digital PCR Reveals a Higher than Expected Fraction of Fetal DNA in Maternal Plasma", Molecular Diagnostics and Genetics, Clinical Chemistry, 2008, 54(10):1664-1672.

Magnasco, Marcelo, O., "Forced Thermal Ratchets", Physical Review Letters, 1993, 71(10):1477-1481.

Makridakis, Nick M., "PCR-free method detects high frequency of genomic instability in prostate cancer", Nucleic Acids Research, 2009, 37(22):7441-7446.

Marziali, A., et al., "Novel electrophoresis mechanism based on synchronous alternating drag perturbation", Electrophoresis 2005, 26:82-90, published on-line Dec. 29, 2004 at URL www.3.interscience.wiley.com/cgi-bin/issue/109861245.

Nollau, Peter, et al., "Methods for detection of point mutations: performance and quality assessment", Department of Clinical Chemistry, 1997, 43(7):1114-1128.

Office Action mailed Aug. 19, 2011 for U.S. Appl. No. 11/815,760.

Office Action mailed Dec. 27, 2010 for U.S. Appl. No. 11/815,760.

Pel, J., "A novel electrophoretic mechanism and separation parameter for selective nucleic acid concentration based on synchronous coefficient of drag alteration (SCODA)", (Ph.D. Thesis), Vancouver: University of British Columbia, 2009.

Pel, J., et al., "Nonlinear electrophoretic response yields a unique parameter for separation of biomolecules", PNAS 2009, vol. 106, No. 35, 14796-14801.

Rousseau, J., et al., "Gel electrophoretic mobility of single-stranded DNA: The two reptation field-dependent factors", Electrophoresis, 2000, 21(8):1464-1470.

Sikora, Aleksandra, et al., "Detection of Increased Amounts of Cell-Free DNA with Short PCR Amplicons", Clinical Chemistry, 2010, 56(1):136-138.

Slater, G.W., et al., "Recent developments in DNA electrophoretic separations", Electrophoresis, 1998, 19 (10):1525-1541.

Slater, G.W., et al., "The theory of DNA separation by capillary electrophoresis", Current Opinion in Biotechnology, 2003, 14:58-64.

Slater, G.W., et al., "Theory of DNA electrophoresis: A look at some current challenges", Electrophoresis, 2000, 21:3873-3887.

So. A., et al., "Efficient genomic DNA extraction from low target concentration bacterial cultures using SCODA DNA extraction technology", Cold Spring Harb Protoc, 2010, 1150-1153; 1185-1198.

Supplementary European Search Report corresponding to EP09706657, May 12, 2011, 2 pages.

Supplementary Partial European Search Report corresponding to EP05706448, May 14, 2012, 3 pages.

Tessier, F. et al., "Strategies for the separation of polyelectrolytes based on non-linear dynamics and entropic ratchets in a simple microfluidic device", Applied Physics A—Materials Science & Processing, 2002, 75:285-291.

Thompson, J.D., et al., "Winnowing DNA for Rare Sequences: Highly Specific Sequence and Methylation Based Enrichment," PLOS One, vol. 7, No. 2, Feb. 15, 2012.

Turmel, C., et al., "Molecular detrapping and band narrowing with high frequency modulation of pulsed field electrophoresis", Nucleic Acids Research, 1990, 18(3):569-575.

Viovy, J.L., "Electrophoresis of DNA and other polyelectrolytes: Physical mechanisms", Review of Modern Physics, 2000, 72(3):813-872.

Wright, Caroline, "Cell-free fetal nucleic acids for non-invasive prenatal diagnosis", Report of the UK export working group, Jan. 2009, 64 pages.

Yobas, L., et al., "Nucleic Acid Extraction, Amplification, and Detection on Si-Based Microfluidic Platforms," IEEE Journal of Solid-State Circuits, vol. 42, No. 8, Aug. 2007, 12 pages.

Marziali, A., et al., "Novel electrophoresis mechanism based on synchronous alternating drag perturbation", Electrophoresis 2005, 26, 82-89.

Baba, Yoshinobu, "Capillary Affinity Gel Electrophoresis", Molecular Biotechnology, 1996, (9):1-11.

International Search Report for PCT/CA2012/050576, Feb. 28, 2013 3 pages.

|  | DC Analysis | | | Phase Lock Analysis | | | |
|---|---|---|---|---|---|---|---|
| Frequency (Hz) | Signal (V) | Noise (V) | DC SNR | Signal | Noise | Phase Lock SNR | Ratio of Phase Lock SNR to DC SNR |
| .033 | .039 | .004 | 9.8 | 186 | 21 | 5.8 | 0.59 |
| .100 | .02 | .005 | 4 | 18.7 | 3.3 | 5.6 | 1.40 |
| .300 | .06 | .014 | 4.3 | 29 | 5 | 5.8 | 1.35 |
| 1 | .022 | .01 | 2.2 | 3 | .5 | 6 | 2.73 |
| 3 | .023 | .01 | 2.3 | N/A | N/A | 1 | 0.43 |

FIGURE 8A

|  | DC Analysis | | | Phase Lock Analysis | | | |
|---|---|---|---|---|---|---|---|
| Number of Cycles | Signal (V) | Noise (V) | DC SNR | Signal | Noise | Phase Lock SNR | Ratio of Phase Lock SNR to DC SNR |
| 0 | .0 | .004 | 2.1 | N/A | N/A | 1 | 0.48 |
| 10 | .063 | .003 | 21 | 128 | 10.8 | 11.9 | .58 |
| 30 | .060 | .003 | 20 | 180 | 10 | 18 | 0.9 |

FIGURE 8B

SYSTEM AND METHODS FOR DETECTION OF PARTICLES

REFERENCE TO RELATED APPLICATION

This application claims Paris convention priority from U.S. patent application No. 61/202,932 filed 21 Apr. 2009 and entitled "Detection system for scodaphoresis" which is hereby incorporated herein by reference. For purposes of the United States of America, this application claims the benefit under 35 U.S.C. §119 of U.S. patent application No. 61/202,932 filed 21 Apr. 2009 and entitled "Detection system for scodaphoresis" which is hereby incorporated herein by reference.

TECHNICAL FIELD

This invention relates to the detection of particles. The invention may be applied, for example, to the detection of biomolecules such as DNA and RNA. Aspects of the invention provide both methods and apparatus that have application in particle detection. A non-limiting example application is the detection of trace amounts of bio-hazard materials such as anthrax spores.

BACKGROUND

Scodaphoresis (or "SCODA") is a technology that may be applied for concentrating and/or separating particles. SCODA may be applied, for example, to DNA, RNA and other molecules. The following background discussion of SCODA is intended to provide examples that illustrate principles of SCODA and is not intended to impose any limitations on the constitution, makeup or applicability of SCODA methods and apparatus generally.

DESCRIPTION OF THE RELATED ART

SCODA is described in the following documents:
1. US Patent Publication No. 2009/0139867 entitled "Scodaphoresis and methods and apparatus for moving and concentrating particles";
2. PCT Publication No. WO2006/081691 entitled "Apparatus and methods for concentrating and separating particles such as molecules";
3. PCT Publication No. WO2009/094772 entitled "Methods and apparatus for particle introduction and recovery";
4. PCT Application No. PCT/CA2009/001648 entitled "Systems and methods for enhanced SCODA";
5. U.S. Provisional Application No. 61/202,932 entitled "Detection system for scodaphoresis," filed 21 Apr. 2009;
6. US Provisional application Ser. No. 61/319,131 entitled "Systems and Methods for enrichment and detection of molecules", filed Mar. 29, 2010;
7. Marziali, A.; Pel, J.; Bizotto, D.; Whitehead, L. A., "Novel electrophoresis mechanism based on synchronous alternating drag perturbation", Electrophoresis 2005, 26, 82-89;
8. Broemeling, D.; Pel, J.; Gunn, D.; Mai, L.; Thompson, J.; Poon, H.; Marziali, A., "An Instrument for Automated Purification of Nucleic Acids from Contaminated Forensic Samples", JALA 2008, 13, 40-48; and
9. Pel, J.; Broemeling, D.; Mai, L.; Poon, H.; Tropini, G.; Warren, R.; Holt, R.; Marziali, A., "Nonlinear electrophoretic response yields a unique parameter for separation of biomolecules", PNAS 2008, vol. 106, no. 35, 14796-14801;
10. J. Pel, D. Broemeling, L. Mai, H.-L. Poon, G. Tropini, R. L. Warren, R. A. Holt and A. Marziali, Proceedings of the National Academy of Sciences, (2009);

all of which are hereby incorporated herein by reference.

SCODA can involve providing a time-varying driving field component that applies forces to particles in some medium in combination with a time-varying mobility-altering field component that affects the mobility of the particles in the medium. The mobility-altering field component is correlated with the driving field component so as to provide a time-averaged net motion of the particles. SCODA may be applied to cause selected particles to move toward a focus area. Some modes of SCODA exploit the fact that certain particles in appropriate media exhibit non-linear responses to electric fields. In such modes, suitable time-varying electric fields can cause certain types of particles to be focused or concentrated at locations within the medium.

In many practical cases, the instantaneous velocity of a particle in a medium under the influence of an electric field is approximated by:

$$\vec{v} = \mu \vec{E} \quad (1)$$

where $\vec{v}$ is the velocity of the particle, $\vec{E}$, is the electric field and $\mu$ is the mobility of the particle in the medium given, at least approximately, by:

$$\mu = \mu_0 + \kappa |\vec{E}| \quad (2)$$

where $\mu_0$ and $\kappa$ are constants. Particles with larger values for $\kappa$ tend to be focused more strongly than particles with smaller values for $\kappa$.

In some cases, SCODA is performed by providing an electrical field having a rotating component and a quadrupole perturbation. The rotating component may be specified, for example, by:

$$E_x = E \cos(\omega \tau) \quad (3)$$

and $$E_y = E \sin(\omega \tau) \quad (4)$$

where E is a magnitude of the electric field component that rotates at an angular frequency $\omega$, and $E_x$ and $E_y$ are respectively x- and y-components of the rotating electrical field. The perturbing quadrupole component may be specified, for example, by:

$$dE_x = -dE_q x \cos(2\omega \tau) \quad (5)$$

and $$dE_y = dE_q y \cos(2\omega \tau) \quad (6)$$

where $dE_x$ and $dE_y$ are respectively x- and y-components of the perturbing electrical field, x and y are distances from an origin at the center of the quadrupole field pattern and $dE_q$ is the intensity coefficient of the perturbing quadrupole field.

With this SCODA field, the average radial velocity of a particle toward a focus location can be shown to be given by:

$$\bar{\vec{v}} = \left( \frac{kEdE_q}{4} \right) \vec{r} \quad (7)$$

where $\vec{r}$ is a vector pointing toward the focus location and having a magnitude equal to the distance of the particle from the focus location.

The size of a spot into which particles can be focused depends upon K as well as on the rate at which the particles can diffuse in the medium as follows:

$$\frac{1}{R} \propto \sqrt{\frac{K}{D}} \quad (9)$$

where R is a radius of the focused spot and D is a diffusion coefficient.

Molecules having large values of $\sqrt{k/D}$ may focus in the medium under SCODA conditions, and are selectively concentrated within smaller radius distances R relative to molecules with smaller values of $\sqrt{k/D}$.

There are a range of applications in which it is desirable to detect trace quantities of certain materials. These include:
testing for the presence of bio-hazards;
testing for the presence of life forms;
forensics;
etc.

There is a need for cost-effective methods and apparatus for testing for the presence of certain materials.

SUMMARY

The invention has a wide range of aspects that may be applied in combination or individually. These aspects include, without limitation, the following.

Apparatus for detecting particles of interest. The apparatus comprises a scodaphoresis medium (which may comprise a gel or other matrix for example); a signal generator connected to apply a cyclic scodaphoresis field to the medium to concentrate particles in the medium into a focus spot; a sensor configured to detect a signal indicative of the presence of the particles in the focus spot; and a phase-sensitive detector connected to receive the signal and configured to perform phase-sensitive detection using a reference signal that is time varying in phase with the cyclic scodaphoresis field. In some embodiments the sensor comprises a camera or other image acquisition system.

Methods for detecting particles, the methods comprising: applying a time varying cyclic scodaphoresis field to particles in a medium, the scodaphoresis field concentrating the particles in a focus spot that cyclically traverses a trajectory in the medium in time with cycles of the scodaphoresis field; generating at least one signal indicative of the presence of the particles in the focus spot, the signal varying in step with the motion of the focus spot along the trajectory; and performing phase-sensitive detection on the signal using as a reference signal a signal that varies in time with the cyclic scodaphoresis field. Such methods may be capable of detecting trace quantities of target particles (i.e. particles of interest) with relatively high signal to noise ratios.

Methods and apparatus for automatically controlling the positions of focus spots in scodaphoresis apparatus involving acquiring images of a scodaphoresis medium, locating a focus spot by analysis of the images and controlling a scodaphoresis signal generator to move the focus spot to a desired location.

Kits for use in detecting target particles. The kits may comprise medium comprising probes that have a selective affinity for the target particles. The medium may be provided in an assembly comprising a sample well. The kits may comprise a marker having a specific affinity to bind to the target particles. The marker may be disposed in the medium, the sample well or provided separately. In some embodiments the kits comprise configuration parameters stored in machine readable and/or human-readable form for configuring scodaphoresis fields and/or phase-sensitive detection of the target particles.

Methods and apparatus for scodaphoresis which involve sequentially concentrating particles of different types from a single sample or multiple samples in sequential scodaphoresis stages wherein particles of a first type are concentrated to a focus spot under first conditions of temperature and/or scodaphoresis field strength and particles of a second type are concentrated to the focus spot under second conditions of temperature and/or scodaphoresis field strength.

Further aspects of the invention and features of example embodiments of the invention are described below.

BRIEF DESCRIPTION OF THE DRAWINGS

The accompanying drawings illustrate non-limiting example embodiments of the invention. In the drawings, identical reference numbers identify similar elements or acts. The sizes, shapes and relative positions of elements in the drawings are not necessarily to scale. Lengths, angles and distances may not be to scale. Elements may be arbitrarily enlarged and positioned to improve drawing legibility.

FIGS. 8A and 8B are data tables illustrating results of experiments performed using a prototype embodiment.

DETAILED DESCRIPTION

Figure 1:
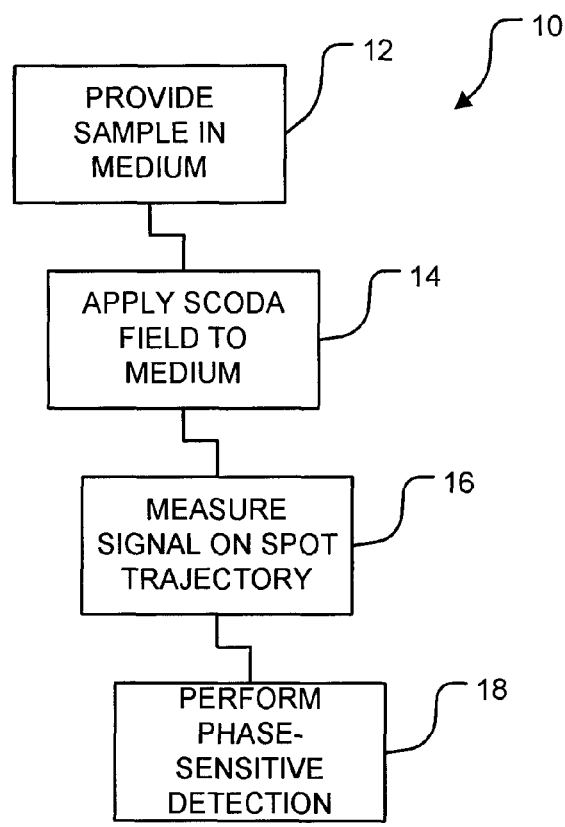
FIG. 1 is a flow chart illustrating a method for detecting particles. In some embodiments the particles comprise DNA.

One aspect of the invention provides methods for detecting particles. In some embodiments the methods are capable of detecting trace amounts of particles such as DNA or RNA. An example method 10 is illustrated in FIG. 1. In block 12 a sample that may contain the particles of interest is provided in a medium. Block 12 may, for example, comprise injection of particles from a fluid sample into the medium under the influence of one or more electric fields. Various methods that may be used to inject particles of interest into a SCODA medium are described in the documents listed under Related Art above. Any suitable procedure may be used to introduce a sample which contains or may contain particles of interest into a SCODA medium.

In block 14 SCODA fields are applied to the medium. The SCODA fields concentrate any particles present in the sample to a focus spot in a focus region of the medium. The location of the focus spot follows a trajectory in the focus region in time with variations in the SCODA fields.

The SCODA fields applied in block 14 may be, for example, of any suitable type as described in any of the documents listed above under Related Art. The SCODA fields may be provided by any suitable mechanism including those described in the documents listed above under Related Art.

In block 16, a signal indicative of the presence of the particles of interest is measured in a region that includes at least a part of the trajectory. In some embodiments block 16 comprises an optical measurement. For example, block 16 may monitor light at wavelengths emitted by and/or absorbed by the particles of interest. In some embodiments, particles of interest can be excited to fluoresce or are marked with a marker that can be excited to fluoresce and the signal is a measurement of the fluorescence of the particles (including any attached fluorescent markers). In some embodiments fluorescence or other emitted light is monitored by imaging the medium with a camera or other imaging array operating in a suitable wavelength band. In such embodiments, pixel values in acquired images constitute signals indicative of the presence of the particles of interest.

In block 18 phase sensitive detection is performed on the signal or signals obtained in block 16. Block 18 may comprise combining the signal or signals with a reference signal that varies in time at a frequency characteristic of the SCODA fields and then integrating the result over time.

Because the particles of interest, if present, are concentrated in the focus spot which the SCODA fields cause to cycle around a trajectory, the signal(s) measured in block 16 are expected to vary with a period characteristic of the SCODA fields. These components of the signal(s) are picked up and amplified by the phase-sensitive detection. By contrast, components of the signal(s) resulting from contamination, noises, or other sources other than the particles of interest that do not vary with a period characteristic of the SCODA fields are reduced or eliminated by the phase-sensitive detection. By coupling phase-sensitive detection to SCODA, which counteracts dispersive forces, one can integrate essentially indefinitely leading to arbitrarily large signal to noise levels.

Figure 2:
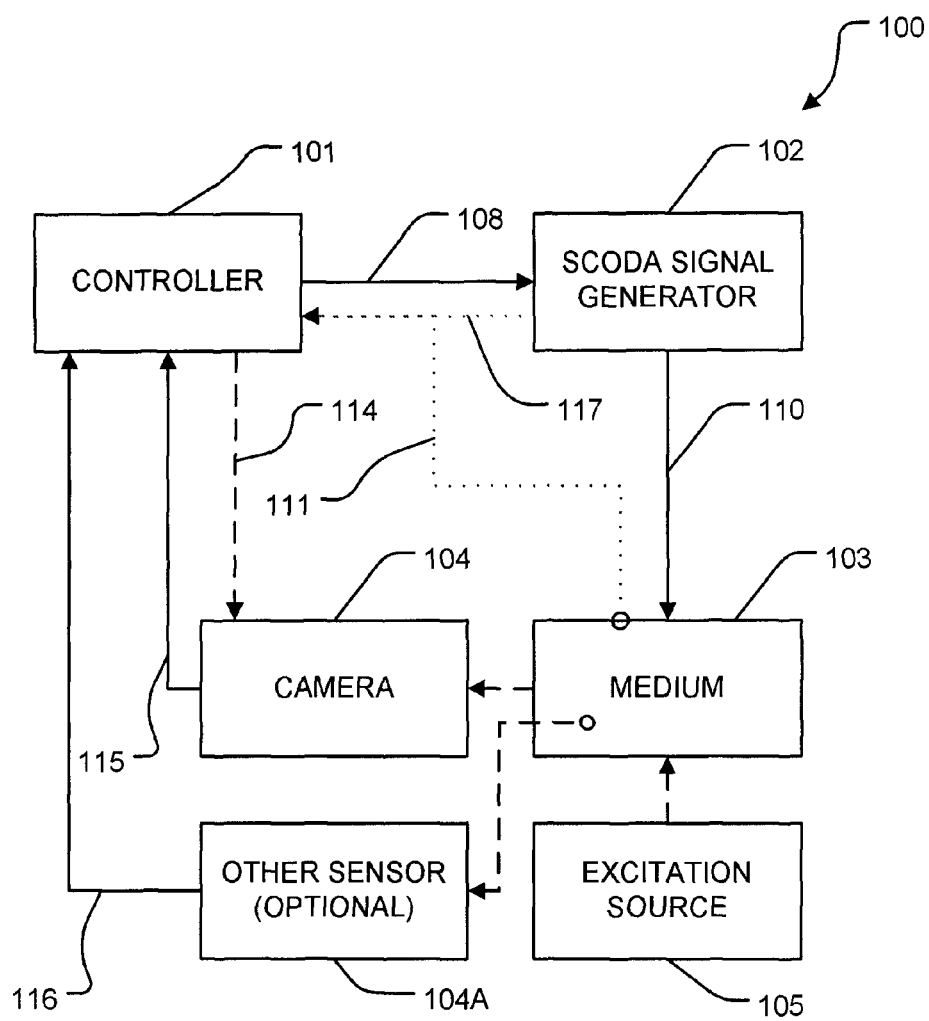
FIG. 2 is a block diagram of an example system which combines SCODA with a phase-sensitive detection scheme.

FIG. 2 shows a system 100 that is operable to apply phase-sensitive detection to detect particles that are being focused using SCODA. A controller 101 controls the overall operation of system 100. Controller 101 may comprise a programmed computer equipped with suitable interfaces, for example. A SCODA signal generator 102 is connected to apply SCODA fields to a medium 103 into which particles may be introduced. Controller 101 causes SCODA signal generator 102 to apply SCODA fields to medium 103.

For example, in some embodiments, signal generator 102 comprises a power supply or amplifier connected to apply electrical fields to medium 103. In such embodiments, controller 101 may generate periodic SCODA signals which may be amplified by signal generator 102 to produce periodic SCODA electrical fields within medium 103. In other embodiments, SCODA signal generator 102 comprises a local hard-wired or programmable controller that generates SCODA signals locally.

Medium 103 may comprise, for example a suitable gel boat containing a gel of a type in which the particles of interest can be focused by SCODA. In some embodiments the gel comprises an agarose gel.

In the illustrated embodiment, SCODA signals are generated in controller 101 and sent to SCODA signal generator 102 on a connection 108. Amplified electric SCODA signals are delivered to medium 103 by connections 110. Feedback from medium 103 may optionally be sent to controller 101 by way of feedback circuitry or connections 111. Where controller 101 is connected to receive feedback signals indicative of SCODA fields being applied in medium 103 for example, by way of feedback connection 111 then controller 101 may incorporate a feedback controller configured to modulate the signals delivered over connection 110 to achieve desired SCODA fields within medium 103. Feedback control of SCODA fields can be useful to accommodate variations in the properties of medium 103. Signals from feedback connection 111 may be applied to adjust SCODA fields so that the SCODA fields will focus any particles of interest at a desired focus region within medium 103.

One or more sensors are provided to detect signals indicative of the presence of particles of interest at location(s) in medium 103. In some embodiments, the sensors comprise a camera 104 located to image at least a portion of medium 103. The imaged portion includes at least a part of the trajectory of SCODA-focused particles in the medium. For example, where the medium 103 comprises a gel boat, a sensor may comprise a camera 104 supported to image a face of the gel boat. The camera may have a field of view that images a small region of medium 103 where concentration of particles occurs due to SCODA focusing.

In some embodiments, camera 104 may comprise one or more high-resolution sensors (such as CCD sensors, CMOS sensors, APS sensors or the like) capable of capturing detailed images of medium 103. Camera 104 may comprise a digital camera interfaced to controller 101. Camera 104 may comprise a video camera or a still image camera, for example. In some embodiments, camera 104 has a sensing array with a resolution of 1 megapixels or greater.

Where the particles of interest fluoresce then a light source 105 may be provided to illuminate medium 103 with light of a wavelength that will cause any particles of interest to fluoresce. Camera 104 may image medium 103 at any suitable wavelengths. In some embodiments camera 104 images medium 104 at visible wavelengths (e.g. in the range of 390 to 750 nm) however, this is not mandatory.

Camera 104 is controlled to repeatedly acquire images of medium 103 during at least two different phases in the application of the periodic SCODA signals by SCODA signal generator 102. In the illustrated embodiment, controller 101 triggers camera 104 by way of signals on connection 114 to acquire images at times corresponding to specific phases of the SCODA field in medium 103. For example, images may be acquired at times corresponding to phases of the SCODA signals that are 180 degrees apart (where the SCODA signals repeat after 360 degrees). For example, images may be acquired at 0 degrees and 180 degrees, or 90 degrees and 270 degrees of the periodic SCODA signals. In some embodiments three or more images are acquired by camera 104 during each cycle of the SCODA signals. For example, images may be acquired at 0 degrees, 90 degrees, 180 degrees and 270 degrees of each cycle of the SCODA signals. It is convenient but not mandatory that the images are acquired at times that are equally-spaced in the SCODA cycle. Images from camera 104 are sent to controller 101 for processing over connection 115.

In other embodiments, camera 104 acquires images periodically and controller 101 associates images acquired from camera 104 with corresponding phases of the SCODA signals. In such embodiments it is not necessary for controller 101 to trigger the acquisition of each image by camera 104.

Optionally system 100 includes one or more other sensors 104A in addition to or instead of camera 104. Other sensors 104A comprise sensors that generate signals indicative of the presence of particles of interest at locations in the trajectory of the SCODA focus spot. For example, where the particles of interest comprise DNA, the other sensors may comprise sensors embedded in medium 103 that directly sense the presence of the DNA or sensors configured to detect a marker attached to the DNA by any suitable modality. A signal or signals from other sensors 104A are delivered to controller 101 by connection 116. Controller 101 may be configured to measure the signal(s) received on connection 116 at times corresponding to specific phases of the SCODA signals being applied to medium 103.

Where controller 101 generates or directly controls the generation of the SCODA signals then controller 101 automatically has information regarding the current phase of the SCODA signals. Additionally or in the alternative controller 101 may receive information regarding the phase of the SCODA signals from sensors associated with medium 103 by way of connection 111 and/or from SCODA signal generator 102 by way of connection 117.

So long as the periodic SCODA fields are applied to medium 103, particles concentrated at the SCODA focus may migrate in an orbit whose radius is determined by the strength and frequency of the applied SCODA fields (for example the electric field strength E and frequency ω in the case of the SCODA fields of Equations (3) to (6), and by properties of the particles. The temporal period of the orbits is determined by the period of the SCODA fields.

Phase-sensitive detection based on the periodic modulation in the position of the SCODA focus spot for particles of interest may be applied to detect the particles of interest. Advantageously, this technique may be applied to detect trace amounts of particles of interest.

In the illustrated embodiment, controller 101 performs phase-sensitive detection on the images received from camera 104 and/or signals received from other sensor(s) 104A. Phase sensitive detection may be performed using a lock-in amplifier or software algorithms, for example. The phase-sensitive detection uses a signal associated with the SCODA signals as a reference signal. The reference signal may be a signal generated or referenced by controller 101 or SCODA signal generator 102 in generating the SCODA signals or a signal derived from measuring SCODA signals at or downstream from the output of SCODA signal generator 102 (e.g. a signal received on connection 111).

Optionally medium 103 includes a component that changes appearance in time with changes in the phase of the SCODA signals applied by SCODA signal generator 102. For example, small lamps or LCD elements in the field of view of camera 104 may be turned on or off or modulated in brightness/density at different times in the cycle of SCODA signals or an element in medium 103 that changes appearance based on an applied electrical field or other SCODA signal may be in the field of view of camera 104. In such embodiments the phase of SCODA signals corresponding to an image from camera 104 may be determined by analysis of the image. This phase information may be applied as a reference signal.

Phase sensitive detection may improve the signal to noise ratio of an input signal by measuring a component of the input signal that has the same frequency and phase as the reference signal. In the present case the position of the concentrated particles or interest is modulated by the SCODA fields. This movement and/or the variation in the amount of signal detected at specific locations in the trajectory of the focused particles may be subject to phase sensitive detection using a reference signal having a fixed phase relationship to the SCODA fields.

One embodiment of the present systems and methods applies optical phase-sensitive detection using a reference signal at the same frequency as the SCODA field rotation and having a fixed phase relationship to the SCODA field rotation. The reference signal may be generated internally in controller 101 (which comprises a computer in some embodiments), Signals from both camera 104 (or another optical detector) and the reference signal are provided to a lock-in amplifier or software carrying out lock-in methods. Those of skill in the art will understand in light of the present specification how to apply known lock-in amplifiers and/or software capable of performing lock-in methods or phase-sensitive detection methods to detect particles as described herein.

Image analysis software capable of analyzing the images of camera 104 and the SCODA signal may be run upon controller 101 or another computer networked to controller 101 such that controller 101 sends the additional computer the reference signal and the images captured by camera 104.

By applying such phase-sensitive optical detection methods an oscillating fluorescent signal from orbiting particles of interest can be coherently detected, and background fluorescence (which will not fluctuate with the SCODA period) will be cancelled during detection.

Figure 3:
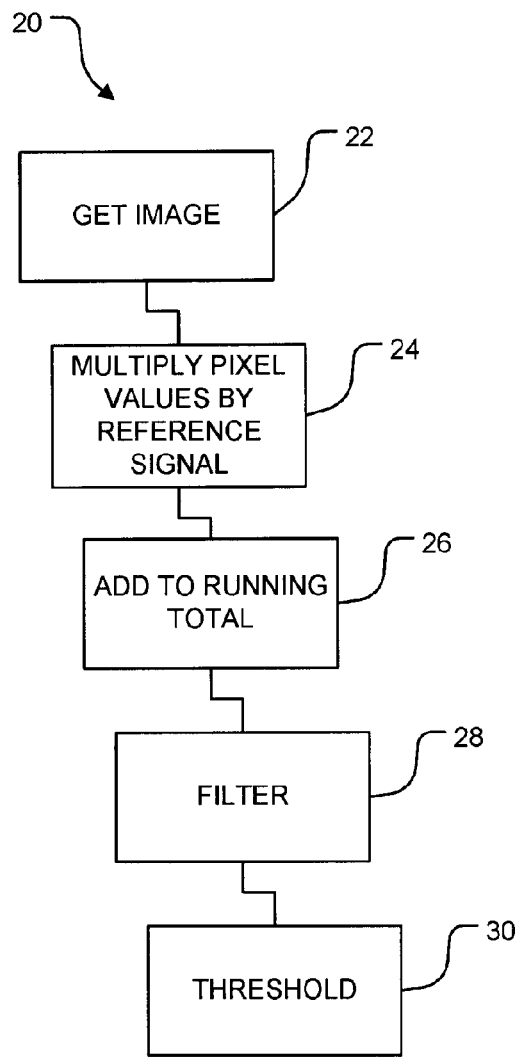
FIG. 3 is a flow chart illustrating a method for phase-sensitive detection of particles based on image data.

FIG. 3 illustrates an example phase-sensitive detection method 20. Image data is acquired in block 22 (for example by receiving an image from camera 104. In block 24 the pixel values in the image are multiplied by the value of a reference signal that varies in time with the SCODA fields. The reference signal may comprise a sinusoidal waveform, for example. Where the images are acquired at specific phases of the SCODA cycle the reference signal may comprise a set of discrete values. For example, where images are acquired twice in any SCODA cycle 180 degrees apart the reference signal may comprise a positive value corresponding to one of the images and an equal negative value corresponding to the other of the images in each cycle.

In block 26 the multiplied pixel values are added to a running total. Separate totals may be kept for each pixel or for groups of pixels within the image. The running total may have a resolution equal to the image data but in some cases the running total has a coarser resolution than the image data.

Figure 3A:
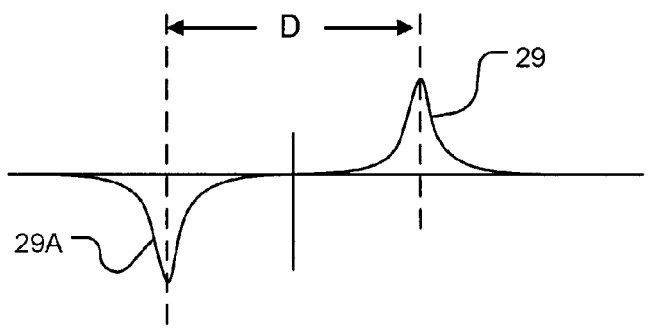
FIG. 3A is a view illustrating a double-Gaussian filter.

In block 28, which is optional, a filter is applied to select a component of the running total image having the expected characteristics of particles. For example the filter may comprise a 2D double Gaussian filter as illustrated in FIG. 3A in which a separation D between peak 29 and inverted peak 29A is equal to the expected radius of the orbit of focused particles of interest.

The location of the SCODA focus spot along its orbit as a function of the phase of the SCODA fields may depend on a combination of characteristics of the particles being focused, characteristics of medium 103, and characteristics of the SCODA fields. For specific particles of interest, this phase relationship may be determined experimentally or estimated theoretically. Where the location of the SCODA focus spot at the phases of analyzed images is known by way of experiment or estimation then the filter applied in block 28 may be oriented so that the centers of peaks 29 and 29A are aligned with the expected locations.

Block 28 may comprise multiplying pixel values in the running total of block 26 by corresponding values of the filter and summing all of the results.

Optionally the output of block 28 is compared to a threshold in block 30. The threshold may be selected so that outputs in excess of the threshold indicate the presence of the particles of interest at the SCODA focus spot.

Figure 4:
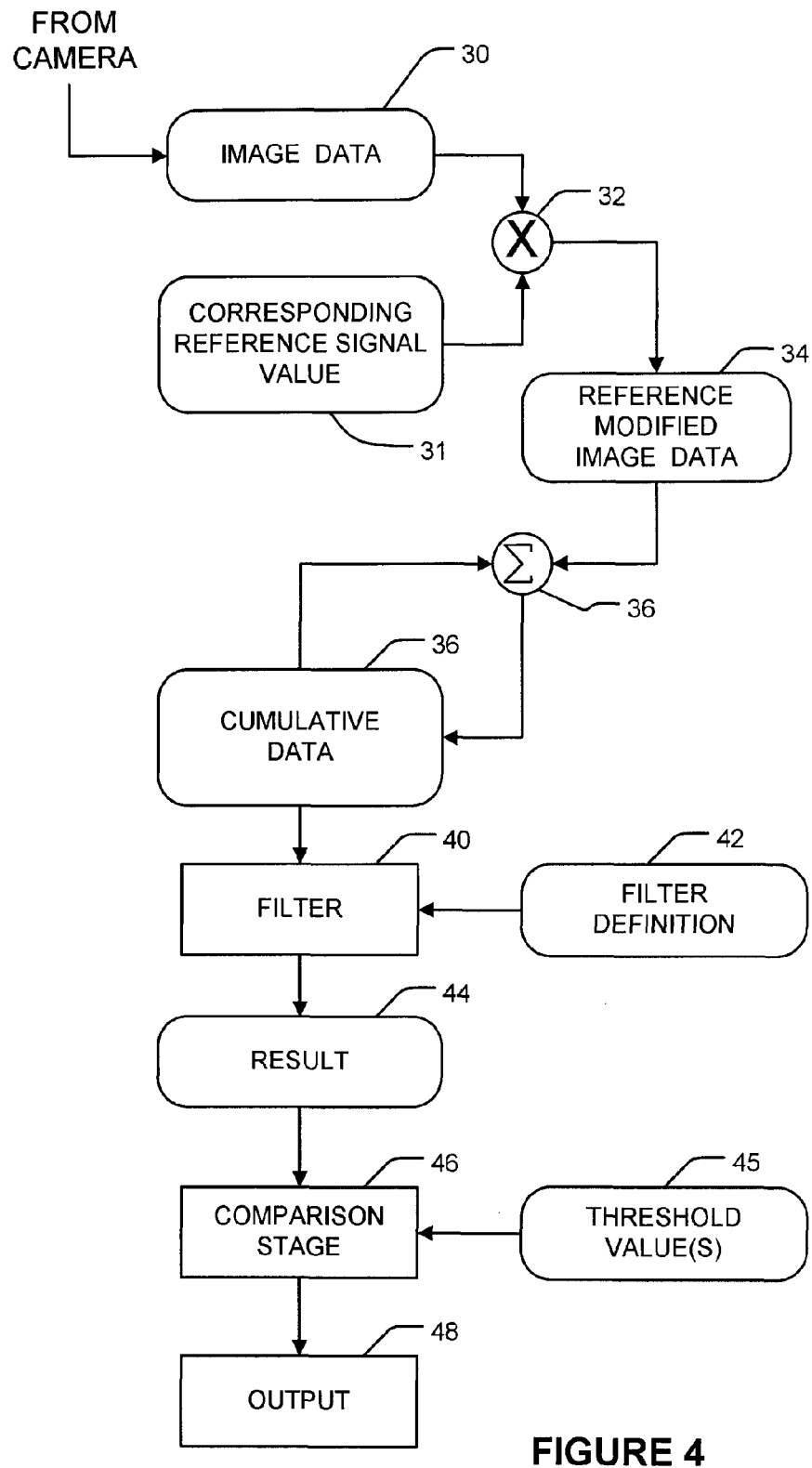
FIG. 4 is a diagram illustrating a data flow in an example controller configured to generate an output indicating detection of particles.

FIG. 4 illustrates data flow in a controller according to an example embodiment. Image data 30 is multiplied by a corresponding reference signal value by a multiplier 32. In some embodiments multiplier 32 multiplies all pixel values in image data for each image by a corresponding reference signal value 31. The resulting reference modified image data 34 is passed to a summing stage 36.

Summing stage 36 sums reference modified image data 34 with cumulative data 38. Periodically or at a desired time, cumulative data 38 is passed to a filter 40 which filters the data applying a filter definition (or kernel) 42 to generate a result 44. Result 44 is passed to a comparison stage 46 which compares result 44 to threshold value(s) 45 to generate a signal that is passed to an output stage 48.

Output stage 48 may perform an action such as: display or store information regarding the detected particles; generate an alarm, generate messages or other communications, etc.

Figure 5A:
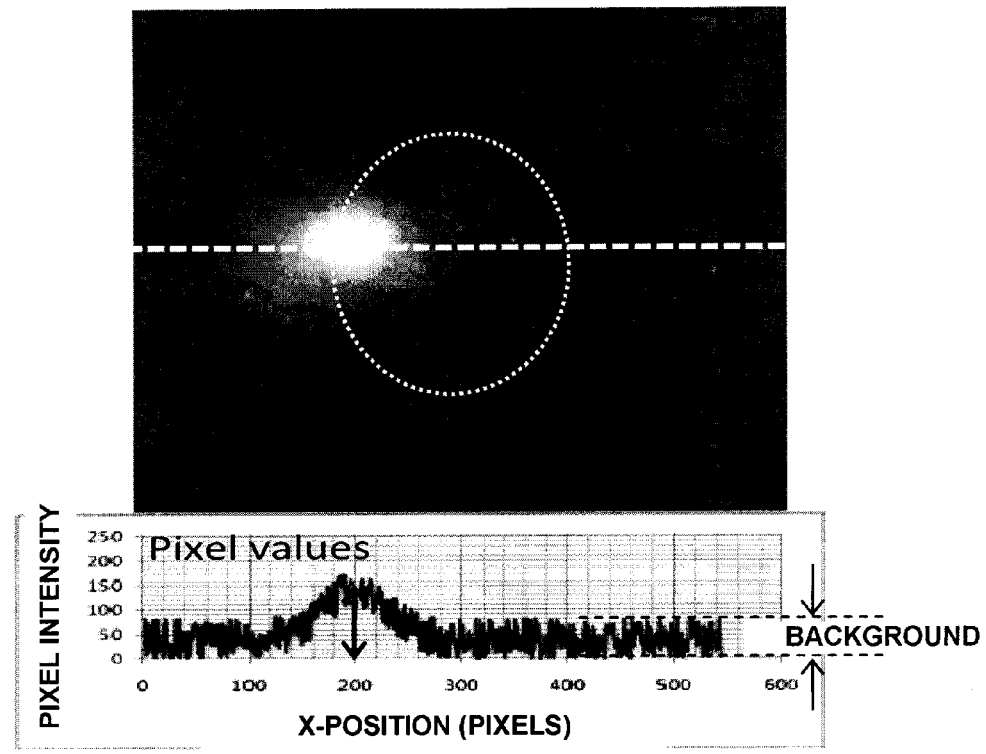
FIGS. 5A, 5B and 5C are example images and graphs illustrating the operation of a phase-sensitive optical detection scheme.

FIG. 5A shows an example combination of several images of focused particles tagged with a dye capable of being detected by a camera. Camera 104 captured these images at a 0 degree phase of the SCODA field. Pixel intensity values along a horizontal line across the center of the image, multiplied by the cosine of the phase of the SCODA field (where cos(0 degrees)=1), is shown in a graph below the image. The height of the signal and the strength of the background noise from the image are shown on the graph. The circular orbit followed by the SCODA focus is also shown in FIG. 5A.

Figure 5B:
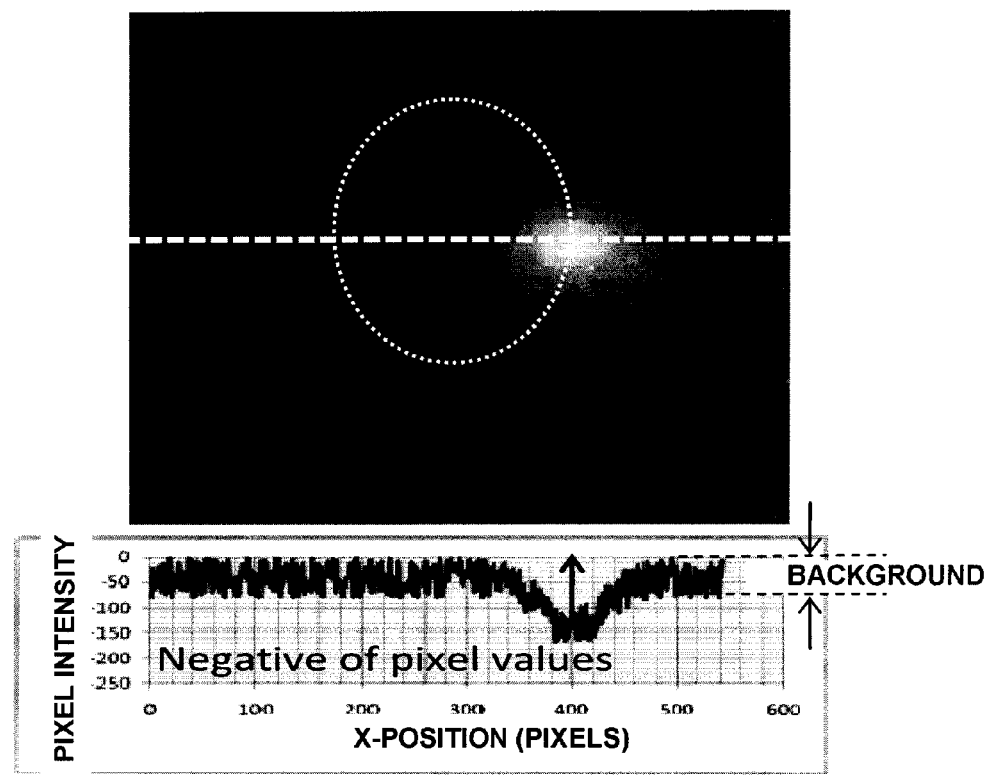

FIG. 5B shows another example combination of several images of focused particles tagged with a dye capable of being detected by a camera. Camera 104 captured these images at a 180 degree phase of the SCODA field. Pixel intensity values along a horizontal line at the center of the image, multiplied by the cosine of the phase of the SCODA field (where cos(180 degrees)=−1), is shown in the graph below the image.

Figure 5C:
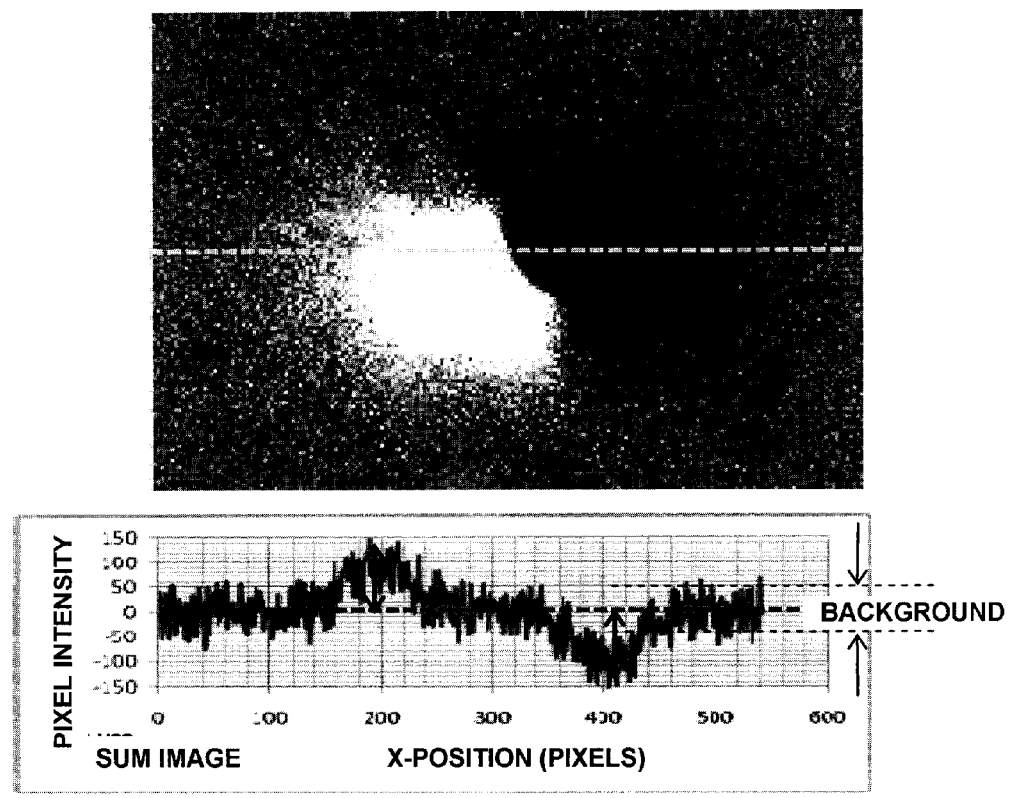

FIG. 5C shows an image resulting from the addition of the images from FIG. 5A and FIG. 5B. The respective pixel intensity values along a horizontal line crossing the center of the image is shown in the graph below the image. If the height of each peak is given by N, the background noise captured with this technique was found to be about the square root of N.

In some embodiments, the signal strength of the detected particles in any one image may be relatively weak and barely detectable or not detectable above the background noise. In such a situation, several images may be taken at 0 and 180 degrees. Such images may be summed to provide an image similar to that of FIG. 5C. The signal from the particles moving with the SCODA focus will constructively add while any background noise will average to zero over a large enough sample set.

To facilitate detection of particles of interest, the particles of interest may be labeled with a detectable marker such as a fluorescent marker before, during, or after SCODA focusing. As the SCODA focusing force may balance diffusive and dispersive forces, there may not be a limit to how long one can integrate the output signal, provided one can detect the particles directly or uses a marker that does not degrade (for example a non-photo bleaching dye may be used to label biomolecules). This leads to the possibility of very high signal to noise ratios even for very low abundance molecules.

Where the particles of interest comprise nucleic acids, labeling may be done with fluorescent-dye labeled nucleic acids that have affinity for the particles of interest. Such labeling can enhance the specificity of the methods described herein since the labels tend not to bind to particles other than particles of interest. Since sequence-specific SCODA may operate at an elevated temperature, it is desirable that nucleic acid labels form a strong bond with the particles of interest.

An example of a specific dye which may be used in the present systems and methods may be an oligonucleotide that is complementary to a target DNA. The oligonucleotide may be labeled with any standard dye using standard attachment chemistries. Examples of dyes include fluorescein, a cyanine dyes (e.g.: cy3, cy5, etc) and rhodamine. These molecules can be made to order at any number of custom oligonucleotide synthesis companies such as Integrated DNA Technologies (www.idtdna.com). The oligonucleotides may be mixed with the target DNA prior to injection, or the oligonucleotides may be washed past a focus spot within a SCODA medium to tag the DNA during or after SCODA focusing. Other examples of labels that may be applied to particles include quantum dots, rare-earth fluorescent dyes and other such labels as known to persons of skill in the art.

In some embodiments it may be desirable to detect the presence of DNA or RNA generally. Such embodiments may involve non-sequence specific labeling of DNA and/or RNA such that any DNA or RNA within a test sample is labeled. Example non-specific dyes include SYBR Green and ethidium bromide. These dyes may bind non-covalently to DNA molecules and fluoresce only when bound to DNA. They have no preference to bind to any particular DNA sequence but tend to bind only DNA. SYBR dyes are available from Invitrogen (www.invitrogen.com) and ethidium bromide is available from chemical suppliers such as Sigma Aldrich (www.sigma.com). These types of dyes may be added to a sample prior to injection into a gel or other medium or added to the gel when it is cast.

In other embodiments involving non-specific labeling, dye molecules (such as fluorescein, cyanine dyes, rhodamine, and the like) may be covalently linked to target DNA prior to injection into a gel or other SCODA medium. In some embodiments, nanoparticles may be used to label target particles. Such nanoparticles may refract light, which may make the labeled target particles detectable by photo detectors, or interact with electromagnetic fields, which may make the labeled particles detectable by an electromagnetic field detector. Still further, biomolecules may be used to tag the particles of interest. Such biomolecules may induce chemical reactions in the SCODA medium proximate to the markers. Changes in chemical composition within the matrix may be detectable by a chemical detector.

As discussed in US Patent Publication No. 2009/0139867 entitled "SCODAPHORESIS AND METHODS AND APPARATUS FOR MOVING AND CONCENTRATING PARTICLES", base-pairing of nucleic acids or other affinity-based interaction between DNA, RNA or other particles of interest and the SCODA medium can enhance SCODA focusing. For example, appropriate choice of oligonucleotides immobilized in a focusing gel can provide SCODA focusing that is selective for certain nucleic acid sequences. This enhancement of SCODA focusing may occur because affinity between particles of interest and the SCODA medium can lead to a strong non-linear relationship between applied field and migration velocity.

In some embodiments SCODA medium 103 includes moieties or other components that have affinity for a particular type or types of particles of interest. In some such embodiments, specificity is increased by treating a sample with a label having a special affinity for the particles of interest.

For analyte molecules that spend some time bound to a matrix of a SCODA medium, the average migration velocity may be proportional to the relative amount of time the analyte molecule spends in its free state. This may be given by:

$$v = \mu(E) * E \frac{t_{on}}{t_{on} + t_{off}} \quad (12)$$

where μ(E) is the field-dependent mobility resulting only from reptation effects; $t_{on}$ is a diffusive binding time (possibly weakly dependent on field) between the migrating analyte and the matrix; and $t_{off}$ is the dissociation time of the matrix-analyte. $t_{on}$, may be adjusted by changing analyte concentration, temperature, and concentration of binding sites in the matrix. $t_{off}$ may be estimated from the Arrhenius relationship:

$$t_{off} = t_d e^{E_b/kT} e^{-\Delta U/kT} \qquad (13)$$

where: $E_b$ is the binding energy between the analyte and the matrix, $\Delta U$ is the decrease in the height of the energy barrier that must be crossed for dissociation, as a result of applied electric force from E, T is the temperature and k is Boltzmann's constant. By inspection, it may be evident that for some regimes (particularly for $t_{on} \sim t_{off}$) the velocity may be exponentially dependent on the extent to which the dissociation barrier is discounted by applied field. A power series expansion of this exponential relation yields a second order term in velocity as a function of electric field, which is the term that drives the SCODA process. In addition to this process, increased electric field may increase power dissipation and gel temperature in specific areas of the gel, further assisting dissociation in parts of the gel subjected to high electric fields.

In embodiments where a target particle comprises a nucleic acid comprising a specific sequence, the SCODA medium may comprise a matrix formed to contain single-stranded nucleic acids that are immobilized and include a partial or perfect complement to the sequence of the target particles of interest.

A SCODA medium may comprise specific probes which bind to specific DNA sequences or other particles of interest. A SCODA medium may comprise a plurality of different probes. Performing SCODA in such a medium may preferentially focus particles having affinity for one or more of the probes. The focused particles may be detected by phase-sensitive detection as described herein.

In some embodiments random hexamers or other materials that have non-specific affinity for nucleic acids may be distributed within a SCODA medium, such as a gel such that any DNA in the gel would bind to the random hexamers. This will increase the speed of SCODA focusing of nucleic acids as the mobility of nucleic acids while strong SCODA fields are present will be very different from the mobility of the nucleic acids while lower SCODA fields are present. During low SCODA fields, DNA may not have enough energy to move within a SCODA medium due to the binding of the nucleic acid with the hexamers. However, during parts of the SCODA cycle where the SCODA field becomes stronger, the nucleic acids may be mobile so that they are driven toward the vicinity of a focal spot.

In some embodiments, the time taken by DNA to bind and unbind to components of a SCODA medium may be of the same time scale as the period of the SCODA field. This may result in phase shifts in the DNA motion which may lead to abnormal focusing or spiraling. By alternating the direction of the SCODA field after a given number of cycles, the spiraling can be cancelled out. The speed of DNA focusing may be reduced due to the continual reversing of direction of the SCODA focusing fields. By changing the phase of the dipole fields, and quadrupole fields should they be present, to account for the phase change due to the timescale interaction, the phase shifts may cancel without any loss in focusing speed. A controller 101 may be configured to automatically control the direction and/or relative phases of the SCODA fields to counteract spiraling.

Methods as described herein, including methods which implement phase-sensitive detection, may be performed to detect target particles of types that are difficult to concentrate using SCODA. For example, proteins may be concentrated, for example as discussed in PCT Application No. PCT/CA2009/001648 entitled "Systems and methods for enhanced SCODA".

As noted above, where the mobility $\mu$ of a type of particle is given, at least approximately, by Equation (2) particles of types having larger values for $\kappa$ tend to be focused more strongly than are particles of types having smaller values for $\kappa$. $\kappa$ may be described as a 'non-linearity coefficient' or a 'coefficient of field dependence of the particle's mobility'. Some embodiments include methods and devices in which the value of $\kappa$ for target particles is increased. In some embodiments, the target particles are biomolecules. In some specific embodiments, the target particles comprise one or more proteins. In some embodiments, the SCODA driving and mobility-altering fields comprise electrical fields.

Process steps that alter $\kappa$ for target particles may comprise one or more of:
  physical treatment which increases $\kappa$ for target particles and/or decreases $\kappa$ for non-target particles;
  chemical treatments which increases $\kappa$ for target particles and/or decreases $\kappa$ for non-target particles; and
  affixation of molecules or other particles to target particles and/or non-target particles that has the effect of increasing $\kappa$ for target particles and/or decreasing $\kappa$ for non-target particles.

Such process steps can alter physical properties of particles (which may be molecules, for example). The altered properties that contribute to the alteration of $\kappa$ may include one or more of (but are not limited to): electric charge, shape, degree of folding, drag, and conformation.

One example of a physical process step that can increase $\kappa$ for a target particle is heat treatment. The heat treatment may include, for example, heating a sample to a temperature and for a period of time sufficient to cause a change in target particles in the sample. In some embodiments the sample is brought to a boil or is heated by thermal contact with a boiling water bath. Heating can be particularly effective for altering $\kappa$ where the target particle is a protein or other molecule that becomes denatured and/or experiences a change in the degree of folding as a result of the heating.

Examples of a chemical process step that can increase $\kappa$ for a target particle are treatment with chemicals that are effective to impart a net electric charge to target particles and/or alter a configuration of the target particles. In some embodiments the target particles are molecules and the chemical treatment denatures and/or changes the degree of folding of the target particle molecules.

The chemical treatment may include, for example, treatment with one or more of: tris-glycine, dithiothreitol, and sodium sodecyl sulfate. In some embodiments the target particles comprise disulfide bonds and the chemical treatment comprises treatment with a chemical that breaks disulfide bonds. In some embodiments the chemical treatment comprises treatment with a detergent such as a suitable anionic surfactant.

Molecules or other particles may be affixed to target particles in various ways. For example, "handle" molecules, having a specific response to SCODA fields, may be attached to "target" molecules by one or more of:
  a linking agent which may comprise, for example, a biomolecule such as an antibody, biotin-avidin complex, an RNA aptamer,
  bonding between the handle and target particles, the bonding may, for example, comprise hydrogen bonding, ionic bonding, or covalent bonding, hydrophobic interactions between the handle and target particles.

other chemical or physical connections.

Target particles to which handle molecules may be attached may comprise, but are not limited to, biomolecules such as proteins, enzymes and nucleic acids such as RNA and DNA. In some example embodiments the handle molecules comprise nucleic acids or proteins (the proteins may be modified so as to be readily focused by a SCODA field). In some embodiments the handle molecules comprise a marker such as a dye or the like.

In some embodiments the handle particles or a linking agent provided to link handle particles to target particles have a specific affinity for particular target particles. For example:

Where the target particles comprise a particular protein, the handle particles may comprise an antibody that interacts specifically with the target particles. The handle particles may comprise, for example, the antibody chemically bonded to a nucleic acid.

Where the target particles comprise a particular DNA or RNA sequence the handle particles may comprise a DNA or RNA sequence that is complementary to the sequence of the target particles.

In such embodiments, a specific protein or other target particle may be moved or concentrated by SCODA fields acting on the handle particles while other particles similar to the target particles which do not bind to the handle particles (or do not bind as strongly to the handle particles) are not concentrated (or not concentrated very much) by the SCODA fields.

Where the handle particles have an affinity for target particles, the handle particles may be attached to the target particles by mixing handle particles into a sample containing the target particles. For example, where the target particles comprise a particular protein, the handle particles may comprise a strand of nucleic acid (e.g. DNA or RNA) linked to an antibody that binds to the protein. The antibody-linked nucleic acid can be mixed with a sample containing the protein targeted by the antibody. The resulting sample can then be processed with SCODA to concentrate the targeted protein at a point in a medium. Such focusing may occur even in cases where the protein itself is electrically neutral or, for some other reason, is not focused very much or at all by the applied SCODA fields.

The foregoing techniques may be applied to improve the selectivity of SCODA focusing for selected target particles and/or to improve the degree to which SCODA focuses target particles. In some embodiments, two or more of the above techniques are applied. For example, in one embodiment a sample is prepared for SCODA by a physical or chemical treatment step which alters target particles followed by a process step which selectively attaches handle particles to the altered target particles. The altered target particles are then concentrated by SCODA. The altered target particles may then be identified by phase-sensitive detection as described herein.

Under suitable preparation/lysis conditions, SCODA may be applied to concentrate target particles such as biomolecules (e.g. molecules of nucleic acid, proteins, enzymes and the like) from a wide range of samples. The samples may include, for example, human or animal samples including: blood, tissue, urine, stool, hair, biopsy, sputum, lavage fluids, discharge, mucus, skin; environmental samples such as: food, water, soil, collected aerosols, plant samples; archeological samples such as: bone, fossil, tar sands, tar pit, ice cores; and so on.

Figure 6:
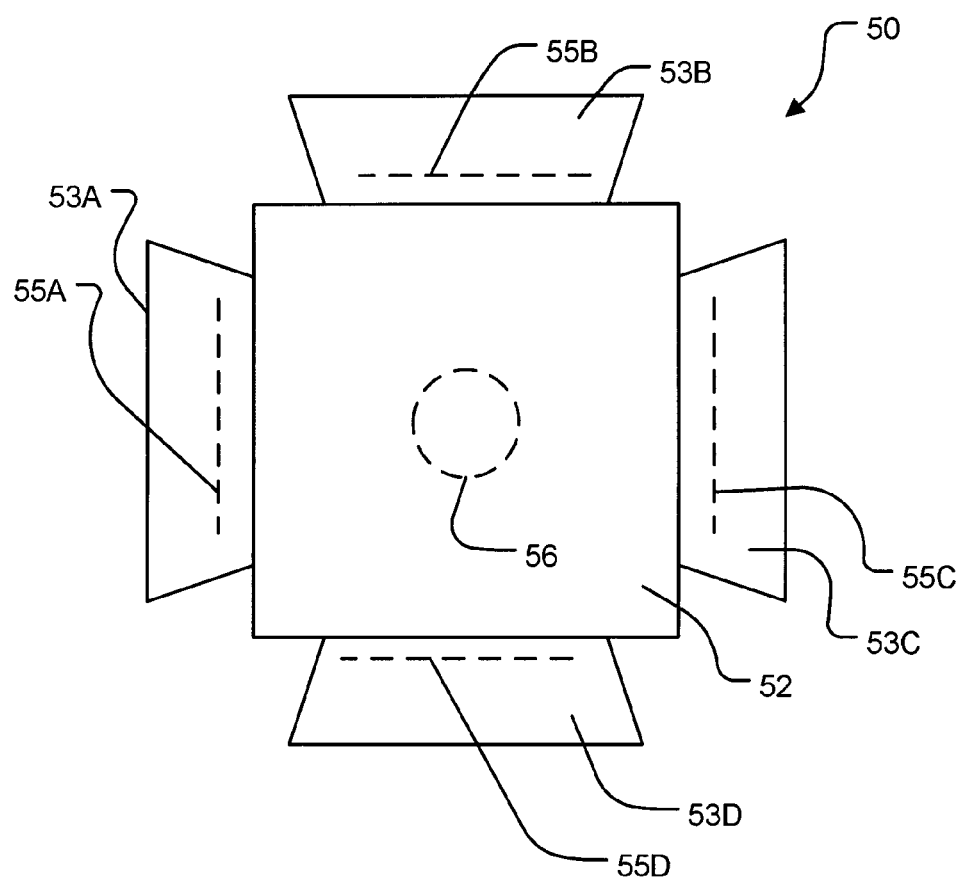
FIG. 6 is a schematic diagram illustrating an example gel boat.
Figure 7:
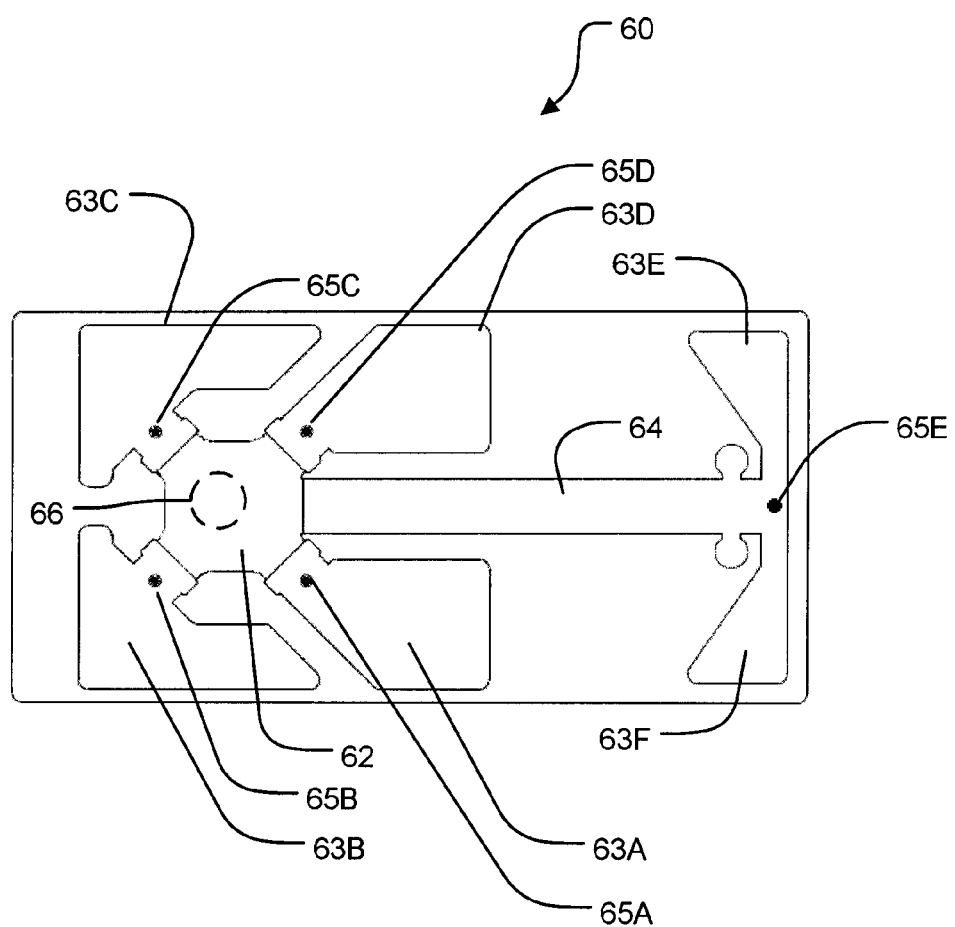
FIG. 7 is a schematic diagram illustrating an example gel boat.

FIGS. 6 and 7 show non-limiting examples of gel boats that may provide SCODA medium 103 in some embodiments. FIG. 6 shows a 4-channel gel boat 50. 4-channel gel boat 50 includes a sheet 52 of gel medium or matrix located amid buffer reservoirs 53A to 53D (collectively buffer reservoirs 53). One buffer reservoir may be located on each side of gel 52. Electrodes 55A to 55D (collectively electrodes 55) are each immersed in a corresponding one of the buffer reservoirs 53. Electrodes 55A to 55D are connected to different channels of a SCODA signal generator 102 such as a programmable power supply in communication with controller 101, that applies potentials to electrodes 55 to provide a SCODA field in gel 52.

Particles may be introduced into gel 52 by introducing a sample containing the particles into one of buffer reservoirs 53 (for example, buffer reservoir 53A) and applying a potential difference between the corresponding electrode 55 and one or more other ones of electrodes 55 to create a first electric field directed to cause particles, which may be molecules, in the buffer reservoir 53, to move toward and into gel 52. Either quadrupole or standard electrokinetic injection may be used to inject particles from one of buffer reservoirs 53 into gel 52.

By applying SCODA fields when particles of interest are in gel 52, the particles of interest can be made to collect at a focal spot in a focal region 56. Excess sample not injected into gel 52 within one of the buffer reservoirs 53 may be removed and replaced with clean buffer solution before the application of SCODA fields as the presence of a sample containing non-injected particles may affect the SCODA fields applied to gel 52.

FIG. 7 shows an example of a 5-channel gel boat 60 that may be applied as a SCODA medium 103. 5-channel gel boat 60 includes a sheet 62 of gel medium or matrix located amid buffer reservoirs 63A to 63D and injection reservoirs 63E and 63F with associated injection channel 64. Some embodiments may have only one injection reservoir and other embodiments may have more than two injection reservoirs. In some embodiments of which the illustrated embodiment is an example, injection reservoirs 63E and 63F are in fluid communication to provide a single injection reservoir in fluidic communication with gel 62 by way of injection channel 64. Electrodes 65A to 65D are each immersed in a corresponding one of buffer reservoirs 63A to 63D and electrode 65E is immersed near injection reservoirs 63E and 63F and one end of injection channel 64. Electrodes 65A to 65E are connected to different channels of a SCODA signal generator such as a programmable power supply that applies time-varying patterns of potentials to electrodes 65 to provide at least one of an injection field and a SCODA field in gel 62.

Particles may be introduced into gel 62 by introducing the particles into the injection channel 64, and by applying a potential difference between the electrode 65E and one or more other ones of electrodes 65 (such as electrodes 65B and 65C) to create a first electric field directed to cause particles, which may be molecules, in injection reservoirs 63E and/or 63F and/or injection channel 64 to travel into gel 62. The distance between electrode 65E and gel 62 results in a relatively high impedance during injection. The resulting long field lines facilitate efficient injection of particles into gel 62. After injection, concentration can proceed by applying voltages to electrodes 65A to 65D which cause SCODA fields in gel 62 while putting electrode 65E at high impedance. The sample can be left in the injection channel 64 and injection reservoirs 63E and 63F, as no field generation is required there, eliminating the sample removal step.

By applying SCODA fields to gel 62 when particles of interest are in gel 62, the particles of interest can be made to collect in a focal spot in the vicinity of a focal region 66. Other particles may pass through gel 62 into at least one of buffer reservoirs 63A to 63D.

Gel 62 of 5-channel gel boat 60 is of octagonal geometry. Numerical estimations have show that a regular octagonal geometry may provide an advantageous a balance between injection speed and focusing speed. In the illustrated embodiment, all edges of gel 62 are of equal length. Gel in other embodiments of 5-channel gel boat may have other shapes such as pentagonal, polygonal or other poly-sided shapes.

An advantage of a 5-channel gel boat as illustrated in FIG. 7 is that any contaminants or salts in a sample from which particles of interest are injected into gel 62 are within injection channel 64 and are not in the main path of the concentration fields. Potential adverse effects of such contaminants on the stability of SCODA focusing is reduced. Because contaminants and salts from the sample have a reduced effect on stability in a gel boat like 5-channel boat 60, a desired level of stability may be achieved without voltage or current feedback. By contrast, a 4-channel gel boat such as gel boat 50, may require voltage and/or current feedback to achieve the same levels of stability. Operating without feedback (open loop) permits simpler electronics and a simpler design for the gel boat.

To help improve open loop stability, high salt buffers (such as 2×TBE) may be run in buffer chambers 63A to 63D during concentration with a 0.25×TBE gel 62. This will help reduce the effect of minor changes in conductivity outside the focusing gel. To help reduce the effect of salt diffusing into the SCODA gel from the sample chamber 63E, a small barrier gel may be added in the sample chamber.

In some embodiments, the temperature at which SCODA is run is varied to permit separate identification two or more types of particles from a single sample. Consider the case where a sample contains two types of particles of interest and the two types of particles have different binding energies to the SCODA medium. The temperature of the SCODA system may be reduced to cause particles of a first type (having a lower binding energy) to be focused more efficiently than particles of a second type (having higher) binding energy. Therefore, particles of the first type may be focused by SCODA while particles of the second type remain unfocused. The particles of the first type may be detected by phase-sensitive detection techniques as described herein.

After detection of the first particles (or failure to detect first particles after a determined time, the temperature of the SCODA system may be raised to give more favorable conditions for concentrating the second particles. The second particles may then be focused thereby allowing for the separate detection of the two types of particles from within the single sample. Again, phase-sensitive detection techniques as described herein may be applied to detect the second particles, if present.

The use of temperature control to sequentially focus particles of a plurality of different types may also be applied in embodiments which do not apply phase-sensitive detection techniques. In such embodiments, particles of a plurality of different types may be sequentially concentrated by SCODA and extracted. the particles may, for example, be extracted from a single sample.

In some embodiments, controller 101 includes a temperature controller connected to control a heater and/or a chiller to control the temperature of the SCODA medium. Controller 101 may comprise a temperature sequence that causes the temperature controller to operate the SCODA medium at a sequence of different temperatures.

Separate focusing of particles of first and second types having different binding energies may be performed at a single temperature by varying the strengths of applied SCODA fields. For example, particles of the first type (having a lower binding energy) may be first focused with the application of a lesser SCODA field. Once particles of the first type have been focused (and optionally detected by phase-sensitive techniques and/or extracted), the SCODA field may be increased to allow for the SCODA focusing of the particles of the second type (having a higher binding energy). The particles of the second type may be focused (and optionally detected by phase-sensitive techniques and/or extracted).

Combinatorial labeling may be used to assist in the identification of different particles of interest. Should two or more DNA or RNA samples interact with labeling dyes uniquely, these different dyes may be introduced into a sample and the resulting SCODA detection will determine which DNA or RNA particles are present.

For example, should a particle type A react with a yellow dye, a particle type B react with a blue dye and a particle type C react with both the yellow and blue dyes, particles A, B and C may be tested for in one SCODA analysis run. Where camera 104 comprises a color camera, spectral analysis of the color of the SCODA focus spot may be performed to identify the type(s) of particles present in the focus spot. For example, by examining images to determine which color dye is present at the SCODA focus after concentration, particles A, B or C can be identified through the detection of either a yellow concentrated dye, a blue concentrated dye, or a perceived green concentrated dye (the combination of blue dye and yellow dye) by camera 104.

In some embodiments, phase-sensitive detection is performed separately for image components corresponding to different color bands.

In some embodiments, the relative phase between the SCODA driving field and the oscillation of the optical signal (resulting from the orbiting of the SCODA focus spot) or the location of the focus spot for a particular phase of the SCODA driving field may be used to distinguish between different types of particles. This may be particularly true at higher field frequencies, where molecules may "lag" behind the field rotation frequency. Molecular properties such as relative mobility or non-linear response to electric field can affect where the SCODA focus spot for such molecules will be located at a specific phase of the SCODA driving field.

For instance, concentrated particles with high mobility may move in phase with the driving SCODA fields such that images acquired at a phase of 0 degrees may show the concentrated particles to be focused at a 12-o'clock position. If under the same SCODA fields images acquired at a phase of 0 degrees show a SCODA focus spot at a different position, for example, the 3-o'clock position, it is known that the composition of the particles in the SCODA focus spot must have changed. The location of a SCODA focus spot for a particular phase of the SCODA signals can be used to determine what type of particles have been focused.

In some embodiments, a controller 101 is configured to measure the relationship between the location of a SCODA focus spot and the phase of applied SCODA fields. Image recognition algorithms may be applied to locate the SCODA focus spot in an image.

A wide range of alternatives and variations is possible in the practice of the invention. Some example alternatives and variations are described below.

Rather than using a camera, one or more photo detectors may be positioned in proximity to a focal area within a SCODA medium. The photo detector(s) may be capable of identifying light emitted by florescent-dye tagged DNA or other particles. The orbiting particles may be periodically detected by the photo detector as the SCODA focus in which the particles are concentrated follows a trajectory in response to the time-varying SCODA fields. A signal related to the detection of dye-marked particles by the photo detector(s) may be used by a lock-in amplifier to identify the presence of the particles in the focal area.

In some embodiments a photo sensor is configured to detect fluorescence of the target particles and the photo sensor senses fluorescence in a fluorescence detection region positioned in the SCODA medium such that when target particles are focused, the SCODA focus spot will trace an orbit that passes into and out of the fluorescence detection region. This may provide a modulated signal suitable for lock-in detection, where a SCODA electric field signal (or a signal derived from or of common origination with the SCODA electric field signal) can be used as a reference signal for phase-sensitive detection.

While optical detection of tagged target particles has been discussed herein, any suitable sensor(s) or detection scheme (optical or otherwise) may be used as the detector in a phase-sensitive scheme. For example, particles of interest may be tagged with a chemical tag. An electrochemical detector may be employed to detect the presence of the particles as indicated by the chemical tag. The electrochemical detector may be embedded in or located below the SCODA medium in a location proximate to the focal area. Particles, such as DNA molecules tagged with chemical tags trapped in a circulating SCODA focus may cause the electrochemical detector to produce a periodic signal. Such a periodic signal may be used by a lock-in amplifier in combination with a suitable reference signal to identify the presence of the particles at the focal area.

A wide variety of phase-sensitive detection schemes may be applied to obtain an output signal having a suitable signal to noise ratio. Some such schemes take advantage of the known trajectory of SCODA focus spots containing the desired particles of interest. The trajectory may be determined experimentally (for example, by subjecting a test sample known to contain the particles of interest and observing the trajectory of the SCODA focus spot) or computed based on known characteristics of the particles of interest and the apparatus. In some embodiments multiple images are acquired by a camera 104 in each SCODA cycle. For each image, pixel values within an area corresponding to the expected location of the SCODA focus spot in the image are processed and integrated so that fluorescence or other optical characteristics indicative of the presence of particles of interest in the SCODA focus spot positions for a set of images tend to add up whereas, when integrated over a set of images, signals coming from areas outside of the SCODA focus spot locations tend to cancel.

Some suitable phase-sensitive detection schemes that may be applied comprise taking an input signal (which may comprise for example pixel values, the output of an optical sensor or some other sensor signal), multiplying the input signal by a reference signal (either provided from an internal clock or an external source), and integrating the result over time. In such embodiments the resulting signal may be an essentially DC signal in which contributions from signal components that are not at the same frequency as the reference signal are attenuated.

For a sine reference signal and an input waveform $U_{in}(t)$, the DC output signal $U_{out}(t)$ for an example analog phase-sensitive detector may be given by:

$$U_{out}(t) = \frac{1}{T}\int_{t-T}^{t} \sin[2\pi f_{ref} \cdot s + \phi]U_{in}(s)ds \qquad (14)$$

where $\Phi$ is a phase that can be set on the lock-in (for example set to zero).

The temperature of a SCODA medium such as a gel may increase due to the application of SCODA fields. This temperature increase may interfere with the focusing of specific sequences of DNA or other particles of interest. Thermally conductive, electrically-insulating components, such as alumina, may be added to a gel or other SCODA medium to the thermal conductivity of the SCODA medium. With increased thermal conductivity, stronger SCODA fields may be applied without causing the temperature of the SCODA medium to increase too much. This may facilitate efficient sample concentration.

The expected radius of the trajectory of concentrated particles and the radius of the spot into which particles are focused vary depending upon characteristics of the target particles. Some embodiments comprise examining images from camera 104 to measure the radius R of the SCODA focus spot and/or its trajectory and using this information as an aid to identifying the type of particles concentrated. Controller 101 may be configured to perform such image analysis, for example.

Optical feedback from images sent to computer 101 may take the place of feedback connection 111. For example, by imaging a larger region of SCODA medium 103 than may be desired solely for phase lock detection, a location of a SCODA focus may be found. Controller 101 may be configured to adjust applied SCODA fields to move the location of the SCODA focus to a desired region in the SCODA medium 103 for extraction, imaging for phase lock detection or sensing by an alternative sensor for phase-sensitive detection.

In some embodiments particles from a sample may be concentrated by applying SCODA a first time and then extracted from a SCODA focus. The extracted particles may be subjected to SCODA focusing a second time. Phase-sensitive detection may be applied in one or both SCODA applications. Serial application of SCODA may help in the purification of highly contaminated or diluted samples.

SCODA signal generator 102 may, for example, comprise a power supply capable of producing four or five distinct time-varying potentials (e.g. a four- or five-channel power supply). This allows each electrode 55 or 65 to be independently set to a desired electric potential for a phase in the generation of SCODA fields within medium 103. SCODA may be performed on samples within a gel boat medium 103 by a SCODA signal generator 102 capable of producing outputs in the range on the order of about ±100V, for example. Larger or smaller potentials may be used in some embodiments.

In some simplified embodiments outputs of SCODA signal generator 102 are switchable between a single potential (for example 100V or so) and ground (i.e. about 0V). Larger or smaller potentials may be used in some embodiments. This elevated potential may be applied to a single electrode such as one of electrodes 55A to 55D while the other three electrodes are grounded. The elevated potential may be applied to all four electrodes 55A to 55D in a sequence timed to produce a SCODA field within medium 103. The sequence may provide that the elevated potential is applied to one of electrodes 55 for a longer period in each cycle than it is applied to an electrode 55 on an opposing side of gel 52 to produce a net drift for the particles being acted upon by the SCODA field. Such a power supply may be advantageous in some application by reason of simplicity, compact size and/or low cost.

Working Example

Experiments with a prototype system have demonstrated that a phase sensitive detection scheme of the general nature described herein can be applied to improve the signal to noise ratio in an optical fluorescence detection system. In these experiments, a band of dye-labeled DNA was injected into a polyacrylamide electrophoresis gel. The band was periodically run back and forth through a detection region. The signal to noise ratio for detection of the dye-tagged DNA was measured as a function of the carrier frequency and as a function of the total integration time and compared to DC integration. FIG. 8A includes a table containing experimental data showing that for certain frequencies there is an improvement in signal to noise ratio (SNR) as compared to DC integration. FIG. 8B includes a table containing experimental data showing that the signal to noise ratio increases with integration time.

The results presented in FIGS. 8A and 8B suggest that if an appropriate carrier frequency is chosen and integrated for long enough, the signal to noise ratio of the output of a phase locked detection scheme should exceed that obtained by integrating the signal for the same time. However, as integration time increases, diffusion and dispersion tend to disperse molecules or other particles of interest. This may have the effect of setting an upper limit on integration time.

When phase sensitive detection is performed in combination with SCODA, SCODA focusing may overcome dispersive effects allowing one to continue integrating for arbitrarily long times. This may allow for the detection of tagged molecules with an arbitrarily large signal to noise ratio that is limited only by how long one is willing to integrate for.

In an example embodiment, a kit is provided for use in detecting a particular type of particles of interest. For example, the kit may be for use in detecting the presence of DNA having a particular sequence (which may indicate the possible presence of a particular bio-hazard, type of bacteria, animal or plant species, or the like). The kit comprises a SCODA medium, such as a suitable gel which includes probes having a specific affinity for the target particles. The gel may optionally be provided in a gel boat having a well for receiving a sample to be tested for the presence of the target particles. The kit may additionally comprise a marker (such as a fluorescent material having a special affinity for the target particles). The marker may be provided in the form of a liquid to be mixed with a sample or may be present in the sample well, the gel or the like so that any particles of interest in a sample can come into contact with the marker before or during SCODA concentration.

In some embodiments the kits comprise configuration parameters stored in machine readable and/or human-readable form for configuring a scodaphoresis apparatus to provide suitable scodaphoresis fields and/or suitable phase-sensitive detection of the target particles.

A user may connect the SCODA medium to a suitable SCODA signal generator and prepare a sample by mixing it with a suitable buffer and introducing the sample into the sample well. If the marker is not already provided in the sample well or gel then the user may add the marker to the sample before or after introducing the sample into the sample well. The user then turns on SCODA apparatus which may be configured to inject particles of interest from the sample well into the SCODA medium and apply SCODA fields to concentrate any particles of interest in the SCODA medium into a SCODA focus spot. The apparatus includes a camera and/or other sensors that apply phase-sensitive techniques to look for a signal indicating presence of the particles of interest that has a time variation indicative of the presence of the target particles in the SCODA focus spot. The system provides to the user information indicating whether or not particles of interest have been detected.

Different kits may be supplied for use in detecting target particles of different types. Some kits may be provided for detecting any of a plurality of different types of target particles (for example nucleic acid fragments characteristic of a range of different bio-hazards, nucleic acid fragments characteristic of specific types of plants or specific genetically-modified organisms or the like)

Among other applications, persons of skill in the art would appreciate that both the simple forms of SCODA, as well as the methods described herein, may be applied to molecule extraction, concentration, purification, and/or detection from samples such as blood, urine, stool, nasal fluids, spinal fluid, bronchial alveoal lavage, semen, other body fluids, soil, tar, water including salt water, mud, ice, forensic samples, fabrics, swabs, formalin fixed tissues, archived blood or serum samples, tissue, cell culture, food matrices, residual fluids from food or other treatment, milk, juice of all types, filters, wash water from wetted wall cyclones, environmental samples and all other materials that may contain even small traces of nucleic acids, proteins or other particles of interest.

In this specification:
- Known elements may not be shown or described in detail in the Description to avoid obscuring the disclosure.
- Specific details are provided to facilitate thorough understanding of various disclosed example embodiments. However, embodiments may be practiced without one or more of these specific details, or in other combinations with other methods, components, materials, etc.
- References to "one embodiment" or "an embodiment" or the like mean that a particular feature, structure or characteristic described in connection with the embodiment may be included in at least one embodiment.
- Phrases like "in one embodiment" or "in an embodiment" do not all refer to the same embodiment.
- The particular features, structures, and/or characteristics of the various example embodiments expressly described herein may be combined in any suitable manners to yield additional embodiments. Such additional embodiments may comprise combinations of the features, structures, and/or characteristics of different expressly disclosed embodiments with one another and/or with other technology in any suitable manner.
- Methods and apparatus described in the example embodiments may optionally be modified by adding elements or acts as described in any of the documents listed above under Related Art.
- Functional elements of apparatus as described herein (as may be indicated for example by blocks in block diagrams or schematic illustrations) may be implemented in a wide variety of ways which are not all described herein since implementing such functional elements at a level of detail more specific than is provided herein comes within the routine skill of those skilled in the art. Such functional elements may be implemented individually and/or collectively, by a wide range of hardware, software, firmware, or suitable combinations thereof.

Methods, or processes which embody the invention may include acts performed in a different order, may include additional acts and/or omit some acts that are described as being part of the example embodiments that are explicitly described.

The headings and Abstract of the Disclosure are for convenience only and are not relevant for interpretation of any embodiments or any terms used herein.

Unless the context clearly requires otherwise, throughout the specification including the claims which follow:

the word "comprise" and variations thereof, such as, "comprises" and "comprising" are to be construed in an open, inclusive sense, that is as "including, but not limited to."

the singular forms "a," "an," and "the" include plural referents.

the term "or" is employed in its inclusive sense "and/or".

In general, in the following claims, the terms used should not be construed to limit the claims to the specific embodiments disclosed in the specification and the claims, but should be construed to include all possible embodiments along with the full scope of equivalents to which such claims are entitled.

While a number of example aspects and embodiments have been discussed above, those of skill in the art will recognize certain useful modifications, permutations, additions and sub-combinations thereof. It is intended that the following appended claims and claims hereafter introduced are interpreted broadly to include all such useful modifications, permutations, additions and sub-combinations that are consistent with the wording of the claims themselves.

What is claimed is:

1. A method for detecting nucleic acids, the method comprising:
    applying a time varying cyclic scodaphoresis field to nucleic acids in a medium, the scodaphoresis field concentrating the nucleic acids in a focus spot that cyclically traverses a trajectory in the medium in time with cycles of the scodaphoresis field;
    exposing the nucleic acids to a marker comprising sequence-specific labels;
    generating at least one signal indicative of the presence of the marker in the focus spot, the signal varying in step with the motion of the focus spot along the trajectory; and
    performing phase-sensitive detection on the signal using as a reference signal a signal that varies in time with the cyclic scodaphoresis field.

2. The method of claim 1 wherein the marker comprises a fluorophore and generating the at least one signal comprises detecting optical radiation at a fluorescence wavelength of the fluorophore.

3. The method of claim 1 wherein generating the at least one signal comprises capturing images of the medium.

4. The method of claim 3 wherein capturing the images comprises at least capturing a first image at a first time corresponding to a first phase of the cyclic scodaphoresis field and capturing a second image at a second time corresponding to a second phase different from the first phase of the cyclic scodaphoresis field.

5. The method of claim 4 wherein the first phase and the second phase are separated by more than 160 degrees.

6. The method of claim 5 wherein the first phase and the second phase are separated by approximately 180 degrees.

7. The method of claim 3 wherein the images comprise color images.

8. The method of claim 3 wherein the images comprise images having a resolution of at least 1 Megapixels.

9. The method of claim 3 wherein performing phase-sensitive detection comprises multiplying pixel values in each of the images by a corresponding reference signal value and accumulating sums of the multiplied pixel values.

10. The method of claim 9 comprising filtering the accumulated sums using a double peaked filter.

11. The method of claim 10 wherein the double-peaked filter comprises a double Gaussian filter.

12. The method of claim 1 wherein the marker comprises a chemical tag and generating the at least one signal comprises detecting the chemical tag by way of an electrochemical detector proximate to the trajectory.

13. The method of claim 1 wherein the marker comprises nanoparticles and generating the at least one signal comprises detecting light scattered by the nanoparticles at a photo detector.

14. The method of claim 1 wherein the marker comprises nanoparticles and generating the at least one signal comprises detecting variations in an electromagnetic field proximate to the trajectory.

15. The method of claim 1 wherein the marker comprises biomolecules and generating the at least one signal comprises detecting chemical reactions involving the biomolecules at a location proximate to the trajectory.

16. The method of claim 1 wherein the medium comprises probes having specific affinity for the particles.

17. The method of claim 16 wherein the probes comprise sequence-specific probes.

18. The method of claim 1 comprising determining a radius of the trajectory.

19. The method of claim 1 comprising determining a radius of the focus spot.

20. The method of claim 1 comprising determining a correlation between the position of the focus spot along the trajectory and a phase of the cyclic scodaphoresis field.

21. The method of claim 20 comprising identifying the nucleic acids in the focus spot based at least in part on the correlation.

22. The method of claim 1 comprising injecting the nucleic acids from a sample into the medium through an injection interface.

23. The method of claim 1 comprising periodically reversing a direction of the scodaphoresis field after a number of complete cycles of the scodaphoresis field have been applied.

24. The method of claim 3 comprising generating the reference signal by analysis of the images.

25. The method of claim 1 wherein the nucleic acids comprise first nucleic acids and second nucleic acids and the method comprises controlling a temperature of the medium to have a first value such that the first nucleic acids are concentrated in the focus spot while the second nucleic acids are not concentrated in the focus spot and subsequently controlling the temperature to have a second value such that the second nucleic acids are concentrated in the focus spot.

26. Apparatus for detecting particles of interest, the apparatus comprising:
    a scodaphoresis medium comprising sequence-specific probes;
    a signal generator connected to apply a cyclic scodaphoresis field to the medium to concentrate particles in the medium into a focus spot;
    a sensor configured to detect a signal indicative of the presence of the particles in the focus spot; and
    a phase-sensitive detector connected to receive the signal and configured to perform phase-sensitive detection using a reference signal that is time varying in phase with the cyclic scodaphoresis field.

27. Apparatus according to claim 26 wherein the sensor comprises an image acquisition system located to image the medium.

28. Apparatus according to claim 27 wherein the image acquisition system comprises a digital camera.

29. Apparatus according to claim 27 wherein the image acquisition system comprises a color image acquisition system.

30. Apparatus according to claim 27 wherein the phase-sensitive detector comprises an image processor configured to multiply pixel values in images by corresponding reference signal values and accumulate sums of the multiplied pixel values.

31. Apparatus according to claim 27 comprising a controller configured to adjust the signal generator to adjust a location of a trajectory in response to feedback from the image acquisition system.

32. Apparatus according to claim 26 wherein the medium is in an assembly comprising an injection reservoir in communication with a surface of the medium.

33. Apparatus according to claim 26 wherein the medium comprises hexamers.

34. Apparatus for detecting particles of interest, the apparatus comprising:

a scodaphoresis medium;

a signal generator connected to apply a cyclic scodaphoresis field to the medium to concentrate particles in the medium into a focus spot;

a sensor comprising an image acquisition system configured to image the medium and to detect a signal indicative of the presence of the particles in the focus spot;

a phase-sensitive detector connected to receive the signal and configured to perform phase-sensitive detection using a reference signal that is time varying in phase with the cyclic scodaphoresis field; and a controller configured to adjust the signal generator thereby adjusting a particle trajectory in response to feedback from the image acquisition system.

* * * * *